United States Patent
Knappe et al.

(10) Patent No.: US 10,258,558 B2
(45) Date of Patent: *Apr. 16, 2019

(54) PRODUCT AND METHOD FOR TEMPORARY SHAPING OF KERATIN-CONTAINING FIBERS

(71) Applicant: Henkel AG & Co. KGaA, Duesseldorf (DE)

(72) Inventors: Thorsten Knappe, Schenefeld (DE); Pamela Kaftan, Hamburg (DE); Maria Catalina Bermudez Agudelo, Hamburg (DE); Tim Bethge, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/360,270

(22) Filed: Nov. 23, 2016

(65) Prior Publication Data

US 2017/0165171 A1 Jun. 15, 2017

(30) Foreign Application Priority Data

Dec. 15, 2015 (DE) .................. 10 2015 225 200

(51) Int. Cl.
| | | |
|---|---|---|
| *A61K 8/31* | (2006.01) | |
| *A61K 8/81* | (2006.01) | |
| *A61Q 5/06* | (2006.01) | |
| *A61K 8/91* | (2006.01) | |

(52) U.S. Cl.
CPC .............. *A61K 8/8152* (2013.01); *A61K 8/31* (2013.01); *A61K 8/8147* (2013.01); *A61K 8/91* (2013.01); *A61Q 5/06* (2013.01)

(58) Field of Classification Search
CPC ...... A61K 8/31; A61K 8/8147; A61K 8/8152; A61Q 5/06
See application file for complete search history.

(56) References Cited

U.S. PATENT DOCUMENTS

| | | | | |
|---|---|---|---|---|
| 5,176,898 A | * | 1/1993 | Goldberg | A61K 8/585 424/47 |
| 2008/0178899 A1 | * | 7/2008 | Moenks | A61K 8/046 132/203 |
| 2014/0093469 A1 | | 4/2014 | Mueller et al. | |

FOREIGN PATENT DOCUMENTS

| | | |
|---|---|---|
| EP | 1719499 A1 | 11/2006 |
| EP | 1719500 A1 | 11/2006 |
| EP | 1726331 A1 | 11/2006 |
| WO | 2005012588 A1 | 2/2005 |
| WO | 2012054278 A2 | 4/2012 |

OTHER PUBLICATIONS

ACUDYNE™ Hair Styling Polymers Product Overview (DOW May 2015; 4 pages).*
Preliminary Amendment for U.S. Appl. No. 15/363,393, dated Nov. 29, 2016.
U.S. Appl. No. 15/363,393, dated Nov. 29, 2016.
Intellectual Property Office, Combined Search and Examination Report under Sections 17 and 18(3) for United Kingdom Patent Application No. GB1621165.8 dated Sep. 29, 2017.

* cited by examiner

*Primary Examiner* — Ernst V Arnold
(74) *Attorney, Agent, or Firm* — Lorenz & Kopf, LLP

(57) ABSTRACT

Cosmetic products and methods for temporarily shaping keratin-containing fibers using the cosmetic products are provided herein. A cosmetic product for temporarily shaping keratinic fibers includes a cosmetic preparation. The cosmetic preparation contains at least one copolymer a1) that is constructed from at least the following monomer units: (meth)acrylic acid, (meth)acrylic acid alkyl ester, and (meth) acrylic acid hydroxy alkyl ester. The cosmetic preparation further contains at least one copolymer a2) that is constructed from at least the following monomer units: styrene, and at least one of acrylic acid or methacrylic acid. The proportion by weight of copolymers a1) and a2) with respect to the total weight of the cosmetic preparation is about 1.0 to about 10 wt %.

18 Claims, No Drawings

PRODUCT AND METHOD FOR TEMPORARY SHAPING OF KERATIN-CONTAINING FIBERS

CROSS-REFERENCE TO RELATED APPLICATION

This application claims priority to German Patent Application No. 10 2015 225 200.0, filed Dec. 15, 2015, which is incorporated herein by reference in its entirety.

TECHNICAL FIELD

This disclosure relates to a cosmetic product for setting hair and for the temporary reshaping of keratinic fibers, particularly human hairs, the composition containing a combination of two specific copolymers.

BACKGROUND

The temporary structuring of hairstyles for an extended period of time lasting up to several days generally requires the use of setting agents. Hair treatment products that serve to temporarily shape the hair therefore play an important role. Such products for temporary shaping usually contain synthetic polymers and/or waxes as the setting agent. Products for supporting the temporary reshaping of keratin-containing fibers can be manufactured as hair spray, hair wax, hair gel, or styling mousse, for example.

The most important characteristic of a product for temporarily shaping hair, hereinafter also called styling product, is that the greatest possible hold is given to the treated fibers in their newly modeled shape—i.e., a shape that is impressed upon the hair. This is also referred to as a strong hairstyle hold or high holding strength of the styling product. The hairstyle hold is determined substantially by the type and quantity of the setting agents used, although the other components of the styling product can also have an impact.

Besides a high holding strength, styling products must meet a whole series of other requirements. These can be roughly subdivided into characteristics on the hair, characteristics of the respective formulation, e.g., characteristics of sprayed aerosols, and characteristics pertaining to the handling of the styling product, with particularly importance being placed on the characteristics on the hair. Particularly noteworthy are moisture resistance, low stickiness (tack), and a balanced conditioning effect. Moreover, a styling product should, to the greatest possible extent, be universally usable for all hair types and be gentle on hair and skin.

In order to meet the various requirements, a multitude of synthetic polymers have already been developed that are used as setting agents in styling products. These polymers can be subdivided into cationic, anionic, nonionic and amphoteric setting polymers.

European patents EP 1719499 B1, EP 1719500 B1 and EP 1726331 B1 describe acrylate resins with INCI designation acrylates/hydroxy ester acrylates copolymer and the use thereof in styling products. International patent application WO 2012/054278 A2 also mentions acrylates/hydroxy ester acrylates copolymers as hair-setting polymers and uses Acudyne® 1000 (The Dow Chemical Company) in styling mousses as an example.

Hair-setting products based on copolymers of styrene with (meth)acrylic acid and/or esters thereof are described in international patent application WO2012/168035 A1.

In principle, not every polymer and not every polymer blend is suitable for the manufacture of hair styling products. This is particularly true of hair sprays, in which the viscosity and therefore also the spraying behavior is influenced by the polymer and the quantity of polymer used, for example.

Even though suitable polymers and polymer combinations have been developed for use in the area of temporary hair-shaping for quite some time, the results that have been achieved thus far continue to leave room for improvement, particularly with regard to the storage stability, applicability and holding strength of these products. In particular, styling products that are currently available can still be improved in the sense that a good combination of holding strength and long-lasting hold (high-humidity curl retention) is not always sufficiently ensured.

BRIEF SUMMARY

Cosmetic products and methods for temporarily shaping keratin-containing fibers using the cosmetic products are provided herein. In one embodiment, a cosmetic product for temporarily shaping keratinic fibers includes a cosmetic preparation. The cosmetic preparation contains at least one copolymer a1) that is constructed from at least the following monomer units: (meth)acrylic acid, (meth)acrylic acid alkyl ester, and (meth)acrylic acid hydroxy alkyl ester. The cosmetic preparation further contains at least one copolymer a2) that is constructed from at least the following monomer units: styrene, and at least one of acrylic acid or methacrylic acid. The proportion by weight of copolymers a1) and a2) with respect to the total weight of the cosmetic preparation is about 1.0 to about 10 wt %.

In another embodiment, a method for temporarily shaping keratin-containing fibers includes the step of loading keratin-containing fibers with a cosmetic product. The cosmetic product contains at least one copolymer a1) that is constructed from at least the following monomer units: (meth)acrylic acid, (meth)acrylic acid alkyl ester, and (meth)acrylic acid hydroxy alkyl ester. The cosmetic product further contains at least one copolymer a2) that is constructed from at least the following monomer units: styrene, and at least one of acrylic acid or methacrylic acid. The proportion by weight of copolymers a1) and a2) with respect to the total weight of the cosmetic product is about 1.0 to about 10 wt %. The method further includes the step of temporarily fixing the keratin-containing fibers into shape.

DETAILED DESCRIPTION

The following detailed description is merely exemplary in nature and is not intended to limit the invention or the application and uses of the invention. Furthermore, there is not intention to be bound by any theory presented in the preceding background or the following detained description.

It is contemplated herein to make additional suitable polymer combinations available that are characterized by good film-forming and/or setting characteristics, and have a very high holding strength without having to sacrifice flexibility and good moisture resistance—particularly perspiration and water resistance. The polymer combinations were to also be suitable for the manufacture of cosmetic products having a high level of chemical and physical stability and be easy to apply.

This was achieved as contemplated herein through a combination of two specific, mutually different copolymers.

The following is made available by the present disclosure:
1. A cosmetic product for temporarily shaping keratinic fibers, comprising
   a) a cosmetic preparation containing
      a1) at least one copolymer that is constructed from at least the following monomer units:
         (meth)acrylic acid
         (meth)acrylic acid alkyl ester
         (meth)acrylic acid hydroxy alkyl ester;
      a2) at least one copolymer that is constructed from at least the following monomer units:
         styrene
         acrylic acid and/or methacrylic acid,
      wherein the proportion by weight of copolymers a1) and a2) with respect to the total weight of the cosmetic preparation is about 1.0 to about 10 wt %.
2. The cosmetic product according to point 1, wherein the proportion by weight of copolymers a1) and a2) with respect to the total weight of the cosmetic preparation is about 1.5 and about 9.0 wt % and particularly about 2.0 to about 8.0 wt %.
3. The cosmetic product according to any one of the preceding points, wherein the at least one copolymer a1) consists, with respect to its total weight, of at least 90 wt %, preferably at least 95 wt % and particularly at least 97 wt % of the monomers
   (meth)acrylic acid
   (meth)acrylic acid alkyl ester
   (meth)acrylic acid hydroxy alkyl ester.
4. The cosmetic product according to any one of the preceding points, wherein the copolymer a1) bears the INCI designation acrylates/hydroxyesters acrylates copolymer.
5. The cosmetic product according to any one of the preceding points, wherein the preparation contains, with respect to its total weight, about 0.1 to about 9.9 wt %, preferably about 0.5 to about 8.5 wt % and particularly from about 1.0 to about 7.0 wt % copolymer a1).
6. The cosmetic product according to any one of the preceding points, wherein the at least one copolymer a2) consists, with respect to its total weight, of at least 90 wt %, preferably at least 95 wt % and particularly at least 97 wt % of the monomers
   styrene
   acrylic acid and/or methacrylic acid.
7. The cosmetic product according to any one of the preceding points, wherein the at least one copolymer a2) consists, with respect to its total weight, of at least 90 wt %, preferably at least 95 wt % and particularly at least 97 wt % of the monomers
   styrene
   acrylic acid and/or methacrylic acid
   acrylic acid ester and/or methacrylic acid ester.
8. The cosmetic product according to any one of the preceding points, wherein the copolymer a2) bears the INCI designation styrene/acrylates copolymer.
9. The cosmetic product according to any one of the preceding points, wherein the preparation contains, with respect to its total weight, about 0.1 to about 9.9 wt %, preferably about 0.5 to about 8.5 wt % and particularly from about 1.0 to about 7.0 wt % copolymer a2).
10. The cosmetic product according to any one of the preceding points, wherein the weight ratio of copolymer a1) to copolymer a2) is from about 1:7 to about 7:1, preferably from about 1:5 to about 5:1 and particularly from about 1:3 to about 3:1.
11. The cosmetic product according to any one of the preceding points, wherein the preparation contains, with respect to its total weight, about 40 to about 98 wt %, preferably about 60 to about 95 wt % and particularly from about 70 to about 92 wt % polar solvent.
12. The cosmetic product according to any one of the preceding points, wherein the preparation consists, with respect to its total weight, of at least 70 wt %, preferably at least 80 wt % and particularly at least 90 wt % of copolymers a1) and a2), ethanol and/or water.
13. The cosmetic product according to any one of the preceding points, wherein the cosmetic preparation further comprises at least one thickener, preferably from the group of the polymeric organic thickeners.
14. The cosmetic product according to any one of the preceding points, wherein the cosmetic preparation further comprises at least one thickener from the group of the anionic polymeric organic thickeners.
15. The cosmetic product according to any one of the preceding points, wherein the cosmetic preparation further comprises at least one thickener from the group of the anionic polymeric amphiphilic thickeners.
16. The cosmetic product according to any one of the preceding points, wherein the cosmetic preparation further comprises at least one thickener from the group with the INCI designations acrylates/beheneth-25 methacrylate copolymer, acrylates/ceteth-20 itaconate copolymer, acrylates/ceteth-20 methacrylate copolymer, acrylates/laureth-25 methacrylate copolymer, acrylates/palmeth-20 acrylate copolymer, acrylates/palmeth-25 acrylate copolymer, acrylates/palmeth-25 itaconate copolymer and acrylates/steareth-50 acrylate copolymer.
17. The cosmetic product according to any one of the preceding points, wherein the preparation contains, with respect to its total weight, about 0.05 to about 8.0 wt %, preferably about 0.1 to about 5.0 wt % thickener.
18. The cosmetic product according to any one of the preceding points, wherein the product further comprises
   b) at least one propellant.
19. The cosmetic product according to any one of the preceding points, wherein the product further comprises
   b) at least one propellant from the group propane, mixture of propane and butane, dimethyl ether and 1,1-difluoroethane.
20. The cosmetic product according to any one of the preceding points, comprising, with respect to its total weight,
   a) about 30 to about 70 wt % of the cosmetic preparation
   b) about 30 to about 70 wt % propellant.
21. A comprehensive product, comprising
   i) a cosmetic product according to any one of points 1 to 20
   ii) a dispensing device with spray valve.
22. A use of a preparation or of a product according to any one of points 1 to 21 for temporarily shaping keratin-containing fibers, particularly human hair.
23. A method for temporarily shaping keratin-containing fibers, particularly human hair, in which the keratin-containing fibers are loaded with a cosmetic product according to any one of points 1 to 21 and temporarily fixed in their shape.

In the context of the present disclosure, it was surprisingly observed that, by combining two inherently known components that are already used in styling products, improved moisture resistance can be obtained in styling products. Other characteristics usually demanded of styling products, such as long-lasting hold, stiffness and low stickiness, are maintained or are improved. Such a good combination of characteristics could not be expected even with knowledge of the individual components and was surprising. It was observed through experimentation that the combination of the two components yielded a highly superadditive, i.e., synergistic effect with regard to the moisture resistance and holding strength.

As contemplated herein, the term "keratinic fibers" includes furs, wool and feathers, but particularly human hair.

The essential components of the cosmetic product as contemplated herein are the anionic copolymer a1) and the anionic copolymer a2), which is different from the copolymer a1).

The cosmetic preparations as contemplated herein contain an anionic copolymer a1) as the first essential component.

With regard to the manufacturability, applicability and cosmetic effect of cosmetic products as contemplated herein, it has proven advantageous if the proportion by weight of the copolymer a1) with respect to the total weight of the cosmetic preparation a) is about 0.1 to about 9.9 wt %, preferably about 0.5 to about 8.5% and particularly from about 1.0 to about 7.0 wt %.

The copolymer a1) is attributable to the monomers (meth)acrylic acid, (meth)acrylic acid alkyl ester and (meth)acrylic acid hydroxy alkyl ester and, optionally, other monomers.

Preferred copolymers a1) preferably consist of at least 90 wt %, preferably at least 95 wt % and particularly at least 97 wt % of the monomers (meth)acrylic acid, (meth)acrylic acid alkyl ester and (meth)acrylic acid hydroxy alkyl ester. Especially preferred copolymers a1) were obtained exclusively from the monomers (meth)acrylic acid, (meth)acrylic acid alkyl ester and (meth)acrylic acid hydroxy alkyl ester.

The cosmetic products according to another preferred embodiment are characterized in that the at least one copolymer a1) consists, with respect to its total weight, of at least 90 wt %, preferably at least 95 wt % and particularly at least 97 wt % of the monomers
 (meth)acrylic acid
 (meth)acrylic acid alkyl ester
 (meth)acrylic acid hydroxy alkyl ester.

The at least one methacrylic acid can be methacrylic acid or acrylic acid.

The alkyl group of the (meth)acrylic acid alkyl ester is preferably a C1-C8 alkyl group that can be linear or branched. Examples of alkyl groups are methyl, ethyl, propyl, isopropyl, 1-butyl, 2-butyl, iso-butyl, tert-butyl, linear or branched pentyl, linear or branched hexyl, linear or branched heptyl and linear or branched octyl. More preferably, the alkyl group is a C1 to C5 alkyl group. According to one embodiment of the disclosure, two or more (meth)acrylic acid alkyl esters are contained which differ from one another with respect to the carbon number of the alkyl group. For example, a methacrylic acid C1-C3 alkyl ester and an acrylic acid C2-O5 alkyl ester are contained.

The hydroxy alkyl group of the (meth)acrylic acid hydroxy alkyl ester can be a hydroxy C1-C10 alkyl group, preferably a hydroxy C2-C5 alkyl group. In a preferred embodiment, the (meth)acrylic acid hydroxy alkyl ester unit is a (meth)acrylic acid hydroxy alkyl ester.

The proportion of the units (meth)acrylic acid, (meth)acrylic acid alkyl ester and (meth)acrylic acid hydroxy alkyl ester in the acrylate resin a1) can vary within wide limits. The proportion of the (meth)acrylic acid in the acrylate copolymer is preferably about 2 to about 50 wt %, more preferably about 5 to about 30 wt %. The proportion of the (meth)acrylic acid alkyl ester in the acrylate copolymer is preferably 5 to 95 wt %, more preferably about 45 to about 90 wt %. The proportion of the (meth)acrylic acid hydroxy alkyl ester in the acrylate copolymer is preferably about 2 to about 70 wt %, more preferably about 5 to about 30 wt %.

The weight average of the molecular weight of the anionic acrylate copolymer a1) is preferably about 130000 to about 160000, more preferably about 140000 to about 150000, determined by means of gel permeation chromatography (GPC).

The viscosity of the anionic acrylate copolymer a1) used in the cosmetic product with a solids content from 44 to 46 wt % and a pH from about 3.30 to about 4.30 at 25° C. is preferably no more than 150 cPS (Brookfield LV, spindle 1, 60 rpm).

The previously described copolymers a1) are sold by Rohm & Haas, for example, under the name Acudyne® 1000 (INCI designation: acrylates/hydroxyesters acrylates copolymer).

The cosmetic preparations as contemplated herein contain an anionic copolymer a2) as the second essential component.

With regard to the manufacturability, applicability and cosmetic effect of cosmetic products as contemplated herein, it has proven advantageous if the proportion by weight of the copolymer a2) with respect to the total weight of the cosmetic preparation a) is about 0.1 to about 9.9 wt %, preferably about 0.5 to about 8.5% and particularly from about 1.0 to about 7.0 wt %.

The copolymer a2) is attributable to the monomers i) styrene and ii) acrylic acid and/or methacrylic acid and, optionally, other monomers.

Preferred copolymers a2) preferably consist of at least 90 wt %, preferably at least 95 wt % and particularly at least 97 wt % of the monomers styrene and acrylic acid and/or methacrylic acid. Especially preferred copolymers a) were obtained exclusively from the monomers styrene and acrylic acid and/or methacrylic acid.

The cosmetic products according to another preferred embodiment are characterized in that the at least one copolymer a2) consists, with respect to its total weight, of at least 90 wt %, preferably at least 95 wt % and particularly at least 97 wt % of the monomers
 styrene
 acrylic acid and/or methacrylic acid
 acrylic acid ester and/or methacrylic acid ester.

The previously described copolymers a2) are sold by Dow Chemicals, for example, under the name Acudyne® Shine (INCI designation: styrene/acrylates copolymer; CAS number 9010-92-8).

The copolymer a2) is preferably used in the cosmetic preparation in partially neutralized or neutralized form. At least one alkanolamine is preferably used for the neutralization. The alkanolamines that can be used as an alkalizing agent as contemplated herein are preferably selected from primary amines with a $C_2$-$C_6$ alkyl parent having at least one hydroxyl group. Especially preferred alkanolamines are selected from the group consisting of 2-aminoethane-1-ol (monoethanolamine), tris(2-hydroxyethyl)-amine (triethanolamine), 3-aminopropane-1-ol, 4-aminobutane-1-ol, 5-aminopentane-1-ol, 1-aminopropane-2-ol, 1-aminobutane-2-ol, 1-aminopentane-2-ol, 1-aminopentane-3-ol, 1-aminopentane-4-ol, 3-amino-2-methylpropane-1-ol, 1-amino-2-methylpropane-2-ol, 3-aminopropane-1,2-diol, 2-amino-2-methylpropane-1,3-diol. Alkanolamines that are very especially preferred as contemplated herein are selected from the group of 2-aminoethane-1-ol, 2-amino-2-methylpropane-1-ol and 2-amino-2-methyl-propane-1,3-diol. 2-amino-2-methylpropanol has proven to be an especially suitable neutralizing agent. Cosmetic products that are preferred as contemplated herein contain at least one alkanolamine, preferably 2-amino-2-methylpropanol. The 2-amino-2-methylpropanol is preferably used in the cosmetic preparations as contemplated herein in a quantity that does not exceed the quantity required for the neutralization of the copolymer a2). Preferably, the quantities of 2-amino-2-methylpropanol used in the cosmetic preparations as contemplated herein are about 80 to 100%, especially preferably about 90 to 100% and particularly about 95 to 100% of the quantity required for the complete neutralization of the copolymer a2). In a preferred embodiment, the proportion by weight of the 2-amino-2-methylpropanol with respect to the total weight of the cosmetic preparation a) is about 0.1 to about 4.0 wt %, preferably about 0.5 to about 3.0 wt % and particularly about 1.0 to about 2.0 wt %.

The proportion by weight of copolymers a1) and a2) with respect to the total weight of the cosmetic preparation is about 1.0 to about 10 wt %. Preferably, the cosmetic product in which the proportion by weight of copolymers a1) and a2) with respect to the total weight of the cosmetic preparation is about 1.5 and about 9.0 wt % and particularly about 2.0 to about 8.0 wt %.

Besides the total proportion by weight of copolymers a1) and a2), the weight ratio of copolymers a1) and a2) in relation to one another has an influence on the moisture resistance, the holding strength, and the other application characteristics of cosmetic products as contemplated herein. Cosmetic products that are technically especially advantageous are characterized in that the weight ratio of copolymer a1) to copolymer a2) is from about 1:7 to about 7:1, preferably from about 1:5 to about 5:1 and particularly from about 1:3 to about 3:1.

Besides the previously described copolymers a1) and copolymers a2), the cosmetic preparations as contemplated herein can contain other active substances, adjuvants and care ingredients.

A first group of active substances that are preferably used are the film-forming polymers. These film-forming polymers are not identical to the copolymer a1) or copolymer a2) described previously. The proportion by weight of the film-forming polymer with respect to the total weight of the cosmetic preparation is about 0.1 to about 8.0 wt %, preferably about 0.5 to about 6.0 wt % and particularly about 1.0 to about 4.0 wt %.

Nonionic polymers are especially preferably used as film-forming polymers. Some examples of suitable nonionic polymers are:

Vinyl pyrrolidone/vinyl ester copolymers, such as those which are sold under the trade name Luviskol® (BASF), for example. Luviskol® VA 64 and Luviskol® VA 73, each vinyl pyrrolidone/acetate copolymers, are preferred nonionic polymers.

Cellulose ethers, such as hydroxypropyl cellulose, hydroxyethyl cellulose and methylhydroxypropyl cellulose, such as those which are sold under the trade names Culminal® and Benecel® (AQUALON), for example.

Shellac.

Polyvinyl pyrrolidones, such as those which are sold under the name Luviskol® (BASF), for example.

Siloxanes. These siloxanes can be both water-soluble and water-insoluble. Both volatile and nonvolatile siloxanes are suitable, with nonvolatile siloxanes being understood as being such compounds whose boiling point at atmospheric pressure lies above 200° C. Preferred siloxanes are polydialkyl siloxanes, such as polydimethylsiloxane, for example; polyalkylaryl siloxanes, such as polyphenylmethyl siloxane, for example; ethoxylated polydialkyl siloxanes, and polydialkyl siloxanes containing amine or hydroxy groups.

Glycosidically substituted silicones.

Due to their cosmetic effect in combination with the copolymers a1) and a2), film-forming polymers that are preferably used as contemplated herein are particularly the polyvinyl pyrrolidones (INCI designation: PVP) and the vinyl pyrrolidone/vinyl acetate copolymers (INCI designation VP/VA copolymers), with the proportion by weight of these polymers preferably being limited to quantities between about 1.0 and about 10 wt %. Especially preferred cosmetic preparations as contemplated herein are therefore characterized in that they also contain, with respect to their total weight, about 1.0 to about 10 wt % polyvinyl pyrrolidone and/or vinyl pyrrolidone/vinyl acetate copolymer, preferably polyvinyl pyrrolidone. Especially preferred cosmetic preparations have a proportion by weight of the polyvinyl pyrrolidone and/or vinyl pyrrolidone/vinyl acetate copolymer with respect to the total weight of the cosmetic preparation from about 2.0 to about 8.5 wt %, preferably from about 3.0 to about 7.0 wt %.

In summary, with the copolymers a1) and a2) as well as the film-forming polymer a3), cosmetic products that are especially preferred as contemplated herein contain three mutually different polymers.

Protein hydrolysates and/or derivatives thereof can be used as a care ingredient. Protein hydrolysates are product mixtures that are obtained through the acidic, basic or enzymatic decomposition of proteins. As contemplated herein, the term "protein hydrolysates" is understood as also referring to total hydrolysates and to individual amino acids and derivatives thereof, as well as to mixtures of different amino acids. The molecular weight of the protein hydrolysates that can be used as contemplated herein lies between about 75, the molecular weight of glycine, and about 200,000; preferably, the molecular weight is about 75 to about 50,000, and very especially preferably about 75 to about 20,000 Dalton.

Another group of care ingredients are the vitamins, provitamins, vitamin precursors and/or derivatives thereof. Those vitamins, provitamins and vitamin precursors are preferred which are usually associated with groups A, B, C, E, F and H.

Other care ingredients are glycerin, propylene glycol, panthenol, caffeine, nicotinamide, and sorbitol.

In addition to plant extract, mono- or oligosaccharides and/or lipids can also be used as a care ingredient.

The composition of some cosmetic preparations a) in which the proportion by weight of copolymers a1) and a2) with respect to the total weight of the cosmetic preparation is about 1.0 to about 10 wt %, preferably about 1.5 to about 9.0 wt % and particularly about 2.0 to about 8.0 wt %, can be found in the following table. (The data in wt % are in relation to the total weight of the cosmetic product unless indicated otherwise.)

|  | Formula 1 | Formula 2 | Formula 3 | Formula 4 | Formula 5 |
| --- | --- | --- | --- | --- | --- |
| Copolymer a1) * | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |

|  | Formula 6 | Formula 7 | Formula 8 | Formula 9 | Formula 10 |
|---|---|---|---|---|---|
| Acrylates/hydroxyesters acrylates copolymer (INCI) | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Optional additives | ad 100 | ad 100 | ad 100 | ad 100 | ad 100 |

|  | Formula 11 | Formula 12 | Formula 13 | Formula 14 | Formula 15 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Styrene/acrylates copolymer (INCI) | 0.1 to 9.9 | 0.1 to 8.9 | 0.5 to 8.0 | 0.5 to 7.5 | 1.0 to 7.0 |
| Optional additives | ad 100 | ad 100 | ad 100 | ad 100 | ad 100 |

|  | Formula 16 | Formula 17 | Formula 18 | Formula 19 | Formula 20 |
|---|---|---|---|---|---|
| Acrylates/hydroxyesters acrylates copolymer (INCI) | 0.1 to 9.9 | 0.1 to 8.9 | 0.5 to 8.0 | 0.5 to 7.5 | 1.0 to 7.0 |
| Styrene/acrylates copolymer (INCI) | 0.1 to 9.9 | 0.1 to 8.9 | 0.5 to 8.0 | 0.5 to 7.5 | 1.0 to 7.0 |
| Optional additives | ad 100 | ad 100 | ad 100 | ad 100 | ad 100 |

* according to claim 1

The cosmetic preparations as contemplated herein can be packaged in various ways. The proportion by weight and the exact composition of the liquid carrier that may be contained in the cosmetic preparation has a significant influence on the final packaged form of these preparations.

Preferred cosmetic products are based on an aqueous, aqueous/alcoholic or alcoholic carriers. Preferred cosmetic products contain about 40 to about 98 wt %, preferably about 60 to about 95 wt % and particularly about 70 to about 92 wt % polar solvent, preferably polar solvent from the group of water, ethanol and isopropanol.

As mentioned previously, the lower alcohols with 1 to 4 carbon atoms that are usually used for cosmetic purposes, such as ethanol and isopropyl, for example, can be used as alcohols.

Besides these alcoholic solvents, water-soluble cosolvents can still also be used, particularly in combination with water. Examples of especially preferred cosolvents are glycerin and/or ethylene glycol and/or 1,2-propylene glycol, which are preferably used in a quantity from 0 to about 30 wt % with respect to the cosmetic preparation a).

Together with the copolymers a1) and a2) described above, the aqueous, aqueous/alcoholic or alcoholic carriers preferably constitute a substantial component of preparations a) as contemplated herein. Cosmetic preparations are especially preferred which, with respect to their total weight, consist of at least 70 wt %, preferably at least 80 wt % and particularly at least 90 wt % of copolymers a1) and a2), ethanol and/or water.

The composition of some technically advantageous cosmetic preparations a) with liquid carrier in which the proportion by weight of copolymers a1) and a2) with respect to the total weight of the cosmetic preparation is about 1.0 to about 10 wt %, preferably about 1.5 to about 9.0 wt % and particularly about 2.0 to about 8.0 wt %, can be found in the following table. (The data in wt % are in relation to the total weight of the cosmetic product unless indicated otherwise.)

|  | Formula 21 | Formula 22 | Formula 23 | Formula 24 | Formula 25 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Water and/or ethanol | 40 to 98 | 40 to 98 | 60 to 95 | 60 to 95 | 70 to 92 |
| Optional additives | ad 100 | ad 100 | ad 100 | ad 100 | ad 100 |

|  | Formula 26 | Formula 27 | Formula 28 | Formula 29 | Formula 30 |
|---|---|---|---|---|---|
| Acrylates/hydroxyesters acrylates copolymer (INCI) | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Water and/or ethanol | 40 to 98 | 40 to 98 | 60 to 95 | 60 to 95 | 70 to 92 |
| Optional additives | ad 100 | ad 100 | ad 100 | ad 100 | ad 100 |

|  | Formula 31 | Formula 32 | Formula 33 | Formula 34 | Formula 35 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Styrene/acrylates copolymer (INCI) | 0.1 to 9.9 | 0.1 to 8.9 | 0.5 to 8.0 | 0.5 to 7.5 | 1.0 to 7.0 |
| Water and/or ethanol | 40 to 98 | 40 to 98 | 60 to 95 | 60 to 95 | 70 to 92 |
| Optional additives | ad 100 | ad 100 | ad 100 | ad 100 | ad 100 |

-continued

|  | Formula 36 | Formula 37 | Formula 38 | Formula 39 | Formula 40 |
|---|---|---|---|---|---|
| Acrylates/hydroxyesters acrylates copolymer (INCI) | 0.1 to 9.9 | 0.1 to 8.9 | 0.5 to 8.0 | 0.5 to 7.5 | 1.0 to 7.0 |
| Styrene/acrylates copolymer (INCI) | 0.1 to 9.9 | 0.1 to 8.9 | 0.5 to 8.0 | 0.5 to 7.5 | 1.0 to 7.0 |
| Water and/or ethanol | 40 to 98 | 40 to 98 | 60 to 95 | 60 to 95 | 70 to 92 |
| Optional additives | ad 100 | ad 100 | ad 100 | ad 100 | ad 100 |

* according to claim 1

As will readily be understood, not only can the proportion by weight of the liquid carrier vary with respect to the total weight of the cosmetic preparation a), the weight ratio of aqueous to alcoholic carrier can also be changed.

The composition of some technically advantageous cosmetic preparations a) with liquid carrier in which the proportion by weight of copolymers a1) and a2) with respect to the total weight of the cosmetic preparation is about 1.0 to about 10 wt %, preferably about 1.5 to about 9.0 wt % and particularly about 2.0 to about 8.0 wt %, can be found in the following table. (The data in wt % are in relation to the total weight of the cosmetic product unless indicated otherwise.) Corresponding cosmetic preparations are suitable as pump sprays, for example.

Cosmetic Preparations a) with High Ethanol Content

|  | Formula 41 | Formula 42 | Formula 43 | Formula 44 | Formula 45 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Ethanol | 60 to 98 | 60 to 98 | 60 to 98 | 60 to 98 | 60 to 98 |
| Water | 0 to 10 | 0 to 10 | 0 to 10 | 0 to 10 | 0 to 10 |
| Optional additives | ad 100 | ad 100 | ad 100 | ad 100 | ad 100 |

|  | Formula 46 | Formula 47 | Formula 48 | Formula 49 | Formula 50 |
|---|---|---|---|---|---|
| Acrylates/hydroxyesters acrylates copolymer (INCI) | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Ethanol | 60 to 98 | 60 to 98 | 60 to 98 | 60 to 98 | 60 to 98 |
| Water | 0 to 10 | 0 to 10 | 0 to 10 | 0 to 10 | 0 to 10 |
| Optional additives | ad 100 | ad 100 | ad 100 | ad 100 | ad 100 |

|  | Formula 51 | Formula 52 | Formula 53 | Formula 54 | Formula 55 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Styrene/acrylates copolymer (INCI) | 0.1 to 9.9 | 0.1 to 8.9 | 0.5 to 8.0 | 0.5 to 7.5 | 1.0 to 7.0 |
| Ethanol | 60 to 98 | 60 to 98 | 60 to 98 | 60 to 98 | 60 to 98 |
| Water | 0 to 10 | 0 to 10 | 0 to 10 | 0 to 10 | 0 to 10 |
| Optional additives | ad 100 | ad 100 | ad 100 | ad 100 | ad 100 |

|  | Formula 56 | Formula 57 | Formula 58 | Formula 59 | Formula 60 |
|---|---|---|---|---|---|
| Acrylates/hydroxyesters acrylates copolymer (INCI) | 0.1 to 9.9 | 0.1 to 8.9 | 0.5 to 8.0 | 0.5 to 7.5 | 1.0 to 7.0 |
| Styrene/acrylates copolymer (INCI) | 0.1 to 9.9 | 0.1 to 8.9 | 0.5 to 8.0 | 0.5 to 7.5 | 1.0 to 7.0 |
| Ethanol | 60 to 98 | 60 to 98 | 60 to 98 | 60 to 98 | 60 to 98 |
| Water | 0 to 10 | 0 to 10 | 0 to 10 | 0 to 10 | 0 to 10 |
| Optional additives | ad 100 | ad 100 | ad 100 | ad 100 | ad 100 |

* according to claim 1

'Cosmetic Preparations a) with Moderate Ethanol Content

|  | Formula 61 | Formula 62 | Formula 63 | Formula 64 | Formula 65 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Ethanol | 10 to 50 | 15 to 50 | 20 to 50 | 25 to 50 | 30 to 50 |
| Water | 2.0 to 40 | 2.0 to 40 | 2.0 to 40 | 2.0 to 40 | 2.0 to 40 |
| Optional additives | ad 100 | ad 100 | ad 100 | ad 100 | ad 100 |

|  | Formula 66 | Formula 67 | Formula 68 | Formula 69 | Formula 70 |
|---|---|---|---|---|---|
| Acrylates/hydroxyesters acrylates copolymer (INCI) | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |

|  | | | | | |
|---|---|---|---|---|---|
| Ethanol | 10 to 50 | 15 to 50 | 20 to 50 | 25 to 50 | 30 to 50 |
| Water | 2.0 to 40 | 2.0 to 40 | 2.0 to 40 | 2.0 to 40 | 2.0 to 40 |
| Optional additives | ad 100 | ad 100 | ad 100 | ad 100 | ad 100 |
|  | Formula 71 | Formula 72 | Formula 73 | Formula 74 | Formula 75 |
| Copolymer a1) * | 0.1 to 9.9 | 0.1 to 8.9 | 0.5 to 8.0 | 0.5 to 7.5 | 1.0 to 7.0 |
| Styrene/acrylates copolymer (INCI) | 0.1 to 9.9 | 0.1 to 8.9 | 0.5 to 8.0 | 0.5 to 7.5 | 1.0 to 7.0 |
| Ethanol | 10 to 50 | 15 to 50 | 20 to 50 | 25 to 50 | 30 to 50 |
| Water | 2.0 to 40 | 2.0 to 40 | 2.0 to 40 | 2.0 to 40 | 2.0 to 40 |
| Optional additives | ad 100 | ad 100 | ad 100 | ad 100 | ad 100 |
|  | Formula 76 | Formula 77 | Formula 78 | Formula 79 | Formula 80 |
| Acrylates/hydroxyesters acrylates copolymer (INCI) | 0.1 to 9.9 | 0.1 to 8.9 | 0.5 to 8.0 | 0.5 to 7.5 | 1.0 to 7.0 |
| Styrene/acrylates copolymer (INCI) | 0.1 to 9.9 | 0.1 to 8.9 | 0.5 to 8.0 | 0.5 to 7.5 | 1.0 to 7.0 |
| Ethanol | 10 to 50 | 15 to 50 | 20 to 50 | 25 to 50 | 30 to 50 |
| Water | 2.0 to 40 | 2.0 to 40 | 2.0 to 40 | 2.0 to 40 | 2.0 to 40 |
| Optional additives | ad 100 | ad 100 | ad 100 | ad 100 | ad 100 |

* according to claim 1

Cosmetic Preparations a) with Low Ethanol Content

|  | Formula 81 | Formula 82 | Formula 83 | Formula 84 | Formula 85 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Ethanol | 0 to 20 | 0 to 20 | 0 to 20 | 0 to 5.0 | 0 to 5.0 |
| Water | 50 to 97 | 60 to 97 | 60 to 97 | 65 to 97 | 65 to 97 |
| Optional additives | ad 100 | ad 100 | ad 100 | ad 100 | ad 100 |
|  | Formula 86 | Formula 87 | Formula 88 | Formula 89 | Formula 90 |
| Acrylates/hydroxyesters acrylates copolymer (INCI) | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Ethanol | 0 to 20 | 0 to 20 | 0 to 20 | 0 to 5.0 | 0 to 5.0 |
| Water | 50 to 97 | 60 to 97 | 60 to 97 | 65 to 97 | 65 to 97 |
| Optional additives | ad 100 | ad 100 | ad 100 | ad 100 | ad 100 |
|  | Formula 91 | Formula 92 | Formula 93 | Formula 94 | Formula 95 |
| Copolymer a1) * | 0.1 to 9.9 | 0.1 to 8.9 | 0.5 to 8.0 | 0.5 to 7.5 | 1.0 to 7.0 |
| Styrene/acrylates copolymer (INCI) | 0.1 to 9.9 | 0.1 to 8.9 | 0.5 to 8.0 | 0.5 to 7.5 | 1.0 to 7.0 |
| Ethanol | 0 to 20 | 0 to 20 | 0 to 20 | 0 to 5.0 | 0 to 5.0 |
| Water | 50 to 97 | 60 to 97 | 60 to 97 | 65 to 97 | 65 to 97 |
| Optional additives | ad 100 | ad 100 | ad 100 | ad 100 | ad 100 |
|  | Formula 96 | Formula 97 | Formula 98 | Formula 99 | Formula 100 |
| Acrylates/hydroxyesters acrylates copolymer (INCI) | 0.1 to 9.9 | 0.1 to 8.9 | 0.5 to 8.0 | 0.5 to 7.5 | 1.0 to 7.0 |
| Styrene/acrylates copolymer (INCI) | 0.1 to 9.9 | 0.1 to 8.9 | 0.5 to 8.0 | 0.5 to 7.5 | 1.0 to 7.0 |
| Ethanol | 0 to 20 | 0 to 20 | 0 to 20 | 0 to 5.0 | 0 to 5.0 |
| Water | 50 to 97 | 60 to 97 | 60 to 97 | 65 to 97 | 65 to 97 |
| Optional additives | ad 100 | ad 100 | ad 100 | ad 100 | ad 100 |

* according to claim 1

Conceivable packaged forms for cosmetic preparations a) as contemplated herein are creams and lotions as well as gels. In addition, however, these preparations are still also suitable for use in the form of a mousse, foam or spray.

Gel-type cosmetic preparations contain at least one thickener as an additional component. With regard to the manufacturability, applicability and cosmetic effect of cosmetic compositions as contemplated herein, it has proven advantageous if the proportion by weight of the thickener a1) with respect to the total weight of the cosmetic preparation a) is about 0.05 to about 8.0 wt %, preferably about 0.1 to about 5.0 wt %.

Preferred thickeners are selected from the group of the polymeric organic thickeners. The polymeric organic thickeners can be crosslinked or non-crosslinked.

Preferred thickeners are selected from the group of the anionic polymeric organic thickeners. A first group of especially preferred thickeners a2) contain at least one structural unit selected from at least one structural unit of formula (I) or salt forms thereof or at least one structural unit (II) or salt forms thereof,

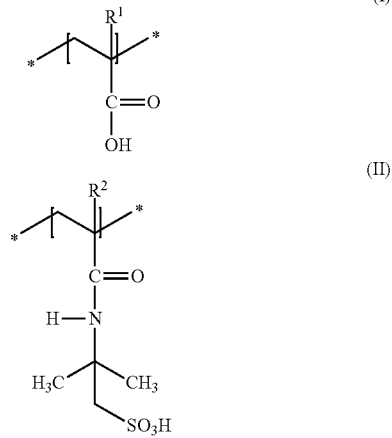

where $R^1$ and $R^2$, independently of one another, stand for a hydrogen atom or a methyl group.

According to the above formulas and all of the following formulas, a chemical bond that is designated with the symbol * stands for a free valance of the corresponding structural fragment.

Especially preferred anionic, thickening polymers contain at least one structural unit of formula (I). Acrylic acid homopolymers constitute a first group of especially preferred thickeners.

Especially preferred thickeners are
polyacrylic acids with the INCI designation carbomer, such as those sold by 3V Sigma under the trade name Synthalen® K or by Lubrizol under the trade name Carbopol, for example.

A second especially preferred group of thickeners a2) is formed by the anionic, polymeric, amphiphilic thickeners. Corresponding thickeners preferably comprise at least one structural unit of formula (III) and at least one structural unit of formula (IV).

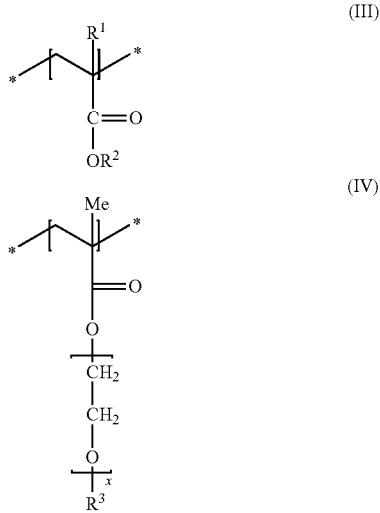

where
$R^1$ stands for a hydrogen atom or a methyl group,
$R^2$ stands for a hydrogen atom or a ($C_1$ bis $C_6$) alkyl group,
$R^3$ stands for a ($C_8$ bis $C_{30}$) alkyl group,
$M^+$ stands for a physiologically acceptable cation, and
x stands for an integer from 0 to 35.

Especially preferred thickeners are particularly those with the INCI designations acrylates/beheneth-25 methacrylate copolymer, acrylates/ceteth-20 itaconate copolymer, acrylates/ceteth-20 methacrylate copolymer, acrylates/laureth-25 methacrylate copolymer, acrylates/palmeth-20 acrylate copolymer, acrylates/palmeth-25 acrylate copolymer, acrylates/palmeth-25 itaconate copolymer and acrylates/steareth-50 acrylate copolymer.

Especially preferred thickeners are
thickeners with the INCI designation acrylates/steareth-20 methacrylate copolymer, such as those sold under the trade name Aculyn® 22 by Rohm&Haas, for example;
thickeners with the INCI designation acrylates/steareth-20 methacrylate crosspolymer, such as those sold under the trade name Aculyn® 88 by Rohm&Haas, for example;
thickeners with the INCI designation acrylates/steareth-20 itaconate copolymer, such as those sold under the trade name Structure 2001 by National Starch, for example;

Other anionic, amphiphilic thickeners are characterized by long-chain alkyl substituents. This group includes the compounds with the INCI designations acrylates/stearyl methacrylate copolymer, acrylates/vinyl isodecanoate crosspolymer.

Especially preferred thickeners are
thickeners with the INCI designation acrylates/$C_{10\text{-}30}$ alkyl acrylate crosspolymer, such as those sold under the trade name Carbopol Ultrez 21 by Lubrizol, for example.

Other thickeners can be selected, for example, from among the polymeric thickening agents known under the following INCI designations: acrylamides copolymer, acrylamide/sodium acrylate copolymer, acrylamide/sodium acryloyldimethyltaurate copolymer, acrylates/acetoacetoxyethyl methacrylate copolymer, acrylic acid/acrylonitrogens copolymer, agar, agarose, alcaligenes polysaccharides, algin, alginic acid, ammonium acrylates/acrylonitrogens copolymer, ammonium acrylates copolymer, ammonium acryloyldimethyltaurate/vinyl formamide copolymer, ammonium acryloyldimethyltaurate/VP copolymer, ammonium alginate, ammonium polyacryloyldimethyl taurate, amylopectin, ascorbyl methylsilanol pectinate, astragalus gummifer gum, attapulgite, avena sativa (oat) kernel flour, bentonite, butoxy chitosan, caesalpinia spinosa gum, calcium alginate, calcium carboxymethyl cellulose, calcium carrageenan, calcium potassium carbomer, calcium starch octenylsuccinate, C20-40 alkyl stearate, carboxybutyl chitosan, carboxymethyl chitin, carboxymethyl chitosan, carboxymethyl dextran, carboxymethyl hydroxyethylcellulose, carboxymethyl hydroxypropyl guar, cellulose acetate propionate carboxylate, cellulose gum, ceratonia siliqua gum, cetyl hydroxyethylcellulose, cholesterol/HDI/pullulan copolymer, cholesteryl hexyl dicarbamate pullulan, cyamopsis tetragonoloba (guar) gum, diglycol/CHDM/isophthalates/SIP copolymer, dihydrogenated tallow benzylmonium hectorite, dimethicone crosspolymer-2, dimethicone propyl PG-betaine, DMAPA acrylates/acrylic acid/acrylonitrogens copolymer, ethylene/sodium acrylate copolymer, gelatin, gellan gum, glyceryl alginate, glycine soja (soybean) flour, guar hydroxypropyltrimonium chloride, hectorite, hydrated silica, hydrogenated potato starch, hydroxybutyl methylcellulose, hydroxyethyl acrylate/sodium acryloyldimethyl taurate copolymer, hydroxyethylcellulose, hydroxyethyl chitosan, hydroxyethyl ethylcellulose, hydroxypropylcellulose, hydroxypropyl chitosan, hydroxypropyl ethylenediamine carbomer, hydroxypropyl guar, hydroxypropyl methylcellulose, hydroxypropyl methylcellulose stearoxy ether, hydroxystearamide MEA, isobutylene/sodium maleate copolymer, lithium magnesium silicate, lithium magnesium sodium silicate, macrocystis pyrifera (kelp), magnesium alginate, magnesium aluminum silicate, magnesium silicate, magnesium trisilicate, methoxy PEG-22/dodecyl glycol copolymer, methylcellulose, methyl ethylcellulose, methyl hydroxyethylcellulose, microcrystalline cellulose, montmorillonite, moroccan lava clay, natto gum, nonoxynyl hydroxyethylcellulose, octadecene/MA copolymer, pectin, PEG-800, PEG-crosspolymer, PEG-150/decyl alcohol/SMDI copolymer, PEG-175 diisostearate, PEG-190 distearate, PEG-15 glyceryl tristearate, PEG-140 glyceryl tristearate, PEG-240/HDI copolymer bis-decyltetradeceth-20 ether, PEG-100/IPDI copolymer, PEG-180/laureth-50/tmmg copolymer, PEG-10/lauryl dimethicone crosspolymer, PEG-15/lauryl dimethicone crosspolymer, PEG-2M, PEG-5M, PEG-7M, PEG-9M, PEG-14M, PEG-20M, PEG-23M, PEG-25M, PEG-45M, PEG-65M, PEG-90M, PEG-115M, PEG-160M, PEG-120 methyl glucose trioleate, PEG-180/octoxynol-40/TMMG copolymer, PEG-150 pentaerythrityl tetrastearate, PEG-4 rapeseedamide, PEG-150/stearyl alcohol/SMDI copolymer, polyacrylate-3, polyacrylic acid, polycyclopentadiene, polyether-1, polyethylene/isopropyl maleate/MA copolyol, polymethacrylic acid, polyquaternium-52, polyvinyl alcohol, potassium alginate, potassium aluminum polyacrylate, potassium carbomer, potassium carrageenan, potassium polyacrylate, potato starch modified, PPG-14 laureth-60 hexyl dicarbamate, PPG-14 laureth-60 isophoryl dicarbamate, PPG-14 palmeth-60 hexyl dicarbamate, propylene glycol alginate, PVP/decene copolymer, PVP montmorillonite, rhizobian gum, ricinoleic acid/adipic acid/AEEA copolymer, sclerotium gum, sodium acrylate/acryloyldimethyl taurate copolymer, sodium acrylates/acrolein copolymer, sodium acrylates/acrylonitrogens copolymer, sodium acrylates copolymer, sodium acrylates/vinyl isodecanoate crosspolymer, sodium acrylate/vinyl alcohol copolymer, sodium carbomer, sodium carboxymethyl chitin, sodium carboxymethyl dextran, sodium carboxymethyl beta-glucan, sodium carboxymethyl starch, sodium carrageenan, sodium cellulose sulfate, sodium cyclodextrin sulfate, sodium hydroxypropyl starch phosphate, sodium isooctylene/MA copolymer, sodium magnesium fluorosilicate, sodium polyacrylate, sodium polyacrylate starch, sodium polyacryloyldimethyl taurate, sodium polymethacrylate, sodium polystyrene sulfonate, sodium silicoaluminate, sodium starch octenylsuccinate, sodium stearoxy PG-hydroxyethylcellulose sulfonate, sodium styrene/acrylates copolymer, sodium tauride acrylates/acrylic acid/acrylonitrogens copolymer, solanum tuberosum (potato) starch, starch/acrylates/acrylamide copolymer, starch hydroxypropyltrimonium chloride, steareth-60 cetyl ether, steareth-100/PEG-136/HDI copolymer, sterculia urens gum, synthetic fluorphlogopite, tamarindus indica seed gum, tapioca starch, TEA-alginate, TEA-carbomer, triticum vulgare (wheat) starch, tromethamine acrylates/acrylonitrogens copolymer, tromethamine magnesium aluminum silicate, welan gum, yeast beta-glucan, yeast polysaccharides, zea mays (corn) starch.

The composition of some technically advantageous cosmetic preparations a) with liquid carrier in which the proportion by weight of copolymers a1) and a2) with respect to the total weight of the cosmetic preparation is about 1.0 to about 10 wt %, preferably about 1.5 to about 9.0 wt % and particularly about 2.0 to about 8.0 wt %, can be found in the following table. (The data in wt % are in relation to the total weight of the cosmetic product unless indicated otherwise.)

|  | Formula 101 | Formula 102 | Formula 103 | Formula 104 | Formula 105 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Polymeric organic thickener | 0.05 to 8.0 | 0.05 to 8.0 | 0.1 to 5.0 | 0.1 to 5.0 | 0.1 to 5.0 |
| Water and/or ethanol | 40 to 98 | 40 to 98 | 60 to 95 | 60 to 95 | 70 to 92 |
| Optional additives | ad 100 | ad 100 | ad 100 | ad 100 | ad 100 |

|  | Formula 106 | Formula 107 | Formula 108 | Formula 109 | Formula 110 |
|---|---|---|---|---|---|
| Acrylates/hydroxyesters acrylates copolymer (INCI) | 0.1 to 9.9 | 0.1 to 8.9 | 0.5 to 8.0 | 0.5 to 7.5 | 1.0 to 7.0 |
| Copolymer a2) * | 0.1 to 9.9 | 0.1 to 8.9 | 0.5 to 8.0 | 0.5 to 7.5 | 1.0 to 7.0 |
| Polymeric organic thickener | 0.05 to 8.0 | 0.05 to 8.0 | 0.1 to 5.0 | 0.1 to 5.0 | 0.1 to 5.0 |
| Water and/or ethanol | 40 to 98 | 40 to 98 | 60 to 95 | 60 to 95 | 70 to 92 |
| Optional additives | ad 100 | ad 100 | ad 100 | ad 100 | ad 100 |

|  | Formula 111 | Formula 112 | Formula 113 | Formula 114 | Formula 115 |
|---|---|---|---|---|---|
| Copolymer a1) * | 0.1 to 9.9 | 0.1 to 8.9 | 0.5 to 8.0 | 0.5 to 7.5 | 1.0 to 7.0 |
| Styrene/acrylates copolymer (INCI) | 0.1 to 9.9 | 0.1 to 8.9 | 0.5 to 8.0 | 0.5 to 7.5 | 1.0 to 7.0 |
| Polymeric organic thickener | 0.05 to 8.0 | 0.05 to 8.0 | 0.1 to 5.0 | 0.1 to 5.0 | 0.1 to 5.0 |
| Water and/or ethanol | 40 to 98 | 40 to 98 | 60 to 95 | 60 to 95 | 70 to 92 |
| Optional additives | ad 100 | ad 100 | ad 100 | ad 100 | ad 100 |

|  | Formula 116 | Formula 117 | Formula 118 | Formula 119 | Formula 120 |
|---|---|---|---|---|---|
| Acrylates/hydroxyesters acrylates copolymer (INCI) | 0.1 to 9.9 | 0.1 to 8.9 | 0.5 to 8.0 | 0.5 to 7.5 | 1.0 to 7.0 |
| Styrene/acrylates copolymer (INCI) | 0.1 to 9.9 | 0.1 to 8.9 | 0.5 to 8.0 | 0.5 to 7.5 | 1.0 to 7.0 |

-continued

| | | | | | |
|---|---|---|---|---|---|
| Polymeric organic thickener | 0.05 to 8.0 | 0.05 to 8.0 | 0.1 to 5.0 | 0.1 to 5.0 | 0.1 to 5.0 |
| Water and/or ethanol | 40 to 98 | 40 to 98 | 60 to 95 | 60 to 95 | 70 to 92 |
| Optional additives | ad 100 | ad 100 | ad 100 | ad 100 | ad 100 |

* according to claim 1

Mousse, foam or spray can be made available both without the addition of a propellant, for example by means of a mechanical pumping, foaming or spraying device, and with the use of a propellant (e.g., aerosol spray). Correspondingly cosmetic products then comprise, in addition to the cosmetic preparation a), at least one propellant b).

Suitable propellants (propellant gases) are propane, propene, n-butane, iso-butane, iso-butene, n-pentane, pentene, iso-pentane, iso-pentene, methane, ethane, dimethylether, nitrogen, air, oxygen, nitrous oxide, 1,1,1,3-tetrafluorethane, heptafluoro-n-propane, perfluorethane, monochlorodifluoromethane, 1,1-difluorethane, both individually and in combination. Hydrophilic propellant gases such as carbon dioxide, for example, can be used advantageously in terms of the present disclosure if the proportion of hydrophilic gases is selected so as to be low and lipophilic propellant gas (e.g., propane/butane) is present in excess. Propane, n-butane, iso-butane and mixtures of these propellant gases are especially preferred. Preferred cosmetic products are characterized in that the product further comprises at least one propellant b) from the group propane, mixture of propane and butane, dimethyl ether and 1,1-difluoroethane (INCI: hydrofluorocarbon 152a).

The rest of the composition of some preferred cosmetic products which, besides the cosmetic preparation a), also comprise a propellant b) and in which the proportion by weight of copolymers a1) and a2) with respect to the total weight of the cosmetic preparation is about 1.0 to about 10 wt %, preferably about 1.5 to about 9.0 wt % and particularly about 2.0 to about 8.0 wt %, can be found in the following tables 1 and 2.

Several preferred cosmetic products containing cosmetic preparation a) and propellant b) are described in the following tables 1 and 2.

Table 1 shows cosmetic products with a low propellant content (e.g., mousses), while table 2 shows cosmetic products with a high propellant content (e.g., sprays).

In tables 1 and 2, the left column ("Formula x") refers to a respective exemplary cosmetic preparation a) of formulas 1 to 100 listed in the tables disclosed further above. The other columns two through five ("Propellant") each indicates the quantity of propellant combined with the corresponding cosmetic preparation. These data in "wt %" are in relation to the total weight of the cosmetic preparation a) of the respective "formula x" without propellant.

In the following table, the indication "4 to 12.5 wt %" therefore corresponds to the addition of propellant to the cosmetic preparation a) in a quantity of about 4 to about 12.5 wt % of the weight of the cosmetic preparation a). In other words, in this cosmetic product, the cosmetic preparation a) and the propellant b) are present in a weight ratio from about 100:4 to about 100:12.5 or from about 25:1 to about 8:1.

To put it another way, the cosmetic products according to line 2, column 4 of the following table 1 are mixtures of the propellant-free cosmetic preparation a) according to formula 1 of the above table with propane/butane in a weight ratio from about 100:4 to about 100:12.5 or, expressed differently, a cosmetic product for temporarily shaping keratinic fibers, comprising a) a cosmetic preparation containing
  a1) about 0.1 to about 9.9 wt % of at least one copolymer that is constructed from at least the following monomer units:
    (meth)acrylic acid
    (meth)acrylic acid alkyl ester
    (meth)acrylic acid hydroxy alkyl ester;
  a2) about 0.1 to about 9.9 wt % of at least one copolymer that is constructed from at least the following monomer units:
    styrene
    acrylic acid and/or methacrylic acid,
b) propellant from the group propane/butane,
wherein the proportion by weight of the copolymers a1) and a2) with respect to the total weight of the cosmetic preparation is about 1.0 to about 10 wt % and the weight ratio of cosmetic preparation a) to propellant b) is about 25:1 to about 8:1.

A first group of especially preferred cosmetic products as contemplated herein contains, with respect to their total weight, about 80 to about 96 wt % of the cosmetic preparation a) and about 4 to about 20 wt % propellant, preferably about 87.5 to about 96 wt % of the cosmetic preparation a) and about 4 to about 12.5 wt % propellant b), and particularly about 92 to about 96 wt % of the cosmetic preparation a) and about 4 to about 8 wt % propellant. Preferred propellants are propane/butane mixtures. Corresponding products are particularly suitable for use as mousse or foam:

TABLE 1

| | Propellant [wt %] | | | |
|---|---|---|---|---|
| Formula 1 | 4 to 20 | 4 to 20 P/B* | 4 to 12.5 P/B* | 4 to 8 P/B* |
| Formula 2 | 4 to 20 | 4 to 20 P/B* | 4 to 12.5 P/B* | 4 to 8 P/B* |
| Formula 3 | 4 to 20 | 4 to 20 P/B* | 4 to 12.5 P/B* | 4 to 8 P/B* |
| Formula 4 | 4 to 20 | 4 to 20 P/B* | 4 to 12.5 P/B* | 4 to 8 P/B* |
| Formula 5 | 4 to 20 | 4 to 20 P/B* | 4 to 12.5 P/B* | 4 to 8 P/B* |
| Formula 6 | 4 to 20 | 4 to 20 P/B* | 4 to 12.5 P/B* | 4 to 8 P/B* |
| Formula 7 | 4 to 20 | 4 to 20 P/B* | 4 to 12.5 P/B* | 4 to 8 P/B* |
| Formula 8 | 4 to 20 | 4 to 20 P/B* | 4 to 12.5 P/B* | 4 to 8 P/B* |
| Formula 9 | 4 to 20 | 4 to 20 P/B* | 4 to 12.5 P/B* | 4 to 8 P/B* |
| Formula 10 | 4 to 20 | 4 to 20 P/B* | 4 to 12.5 P/B* | 4 to 8 P/B* |
| Formula 11 | 4 to 20 | 4 to 20 P/B* | 4 to 12.5 P/B* | 4 to 8 P/B* |
| Formula 12 | 4 to 20 | 4 to 20 P/B* | 4 to 12.5 P/B* | 4 to 8 P/B* |
| Formula 13 | 4 to 20 | 4 to 20 P/B* | 4 to 12.5 P/B* | 4 to 8 P/B* |
| Formula 14 | 4 to 20 | 4 to 20 P/B* | 4 to 12.5 P/B* | 4 to 8 P/B* |
| Formula 15 | 4 to 20 | 4 to 20 P/B* | 4 to 12.5 P/B* | 4 to 8 P/B* |
| Formula 16 | 4 to 20 | 4 to 20 P/B* | 4 to 12.5 P/B* | 4 to 8 P/B* |
| Formula 17 | 4 to 20 | 4 to 20 P/B* | 4 to 12.5 P/B* | 4 to 8 P/B* |
| Formula 18 | 4 to 20 | 4 to 20 P/B* | 4 to 12.5 P/B* | 4 to 8 P/B* |
| Formula 19 | 4 to 20 | 4 to 20 P/B* | 4 to 12.5 P/B* | 4 to 8 P/B* |
| Formula 20 | 4 to 20 | 4 to 20 P/B* | 4 to 12.5 P/B* | 4 to 8 P/B* |
| Formula 21 | 4 to 20 | 4 to 20 P/B* | 4 to 12.5 P/B* | 4 to 8 P/B* |
| Formula 22 | 4 to 20 | 4 to 20 P/B* | 4 to 12.5 P/B* | 4 to 8 P/B* |
| Formula 23 | 4 to 20 | 4 to 20 P/B* | 4 to 12.5 P/B* | 4 to 8 P/B* |
| Formula 24 | 4 to 20 | 4 to 20 P/B* | 4 to 12.5 P/B* | 4 to 8 P/B* |
| Formula 25 | 4 to 20 | 4 to 20 P/B* | 4 to 12.5 P/B* | 4 to 8 P/B* |
| Formula 26 | 4 to 20 | 4 to 20 P/B* | 4 to 12.5 P/B* | 4 to 8 P/B* |
| Formula 27 | 4 to 20 | 4 to 20 P/B* | 4 to 12.5 P/B* | 4 to 8 P/B* |
| Formula 28 | 4 to 20 | 4 to 20 P/B* | 4 to 12.5 P/B* | 4 to 8 P/B* |
| Formula 29 | 4 to 20 | 4 to 20 P/B* | 4 to 12.5 P/B* | 4 to 8 P/B* |
| Formula 30 | 4 to 20 | 4 to 20 P/B* | 4 to 12.5 P/B* | 4 to 8 P/B* |
| Formula 31 | 4 to 20 | 4 to 20 P/B* | 4 to 12.5 P/B* | 4 to 8 P/B* |
| Formula 32 | 4 to 20 | 4 to 20 P/B* | 4 to 12.5 P/B* | 4 to 8 P/B* |

TABLE 1-continued

| | Propellant [wt %] | | | |
|---|---|---|---|---|
| Formula 33 | 4 to 20 | 4 to 20 P/B* | 4 to 12.5 P/B* | 4 to 8 P/B* |
| Formula 34 | 4 to 20 | 4 to 20 P/B* | 4 to 12.5 P/B* | 4 to 8 P/B* |
| Formula 35 | 4 to 20 | 4 to 20 P/B* | 4 to 12.5 P/B* | 4 to 8 P/B* |
| Formula 36 | 4 to 20 | 4 to 20 P/B* | 4 to 12.5 P/B* | 4 to 8 P/B* |
| Formula 37 | 4 to 20 | 4 to 20 P/B* | 4 to 12.5 P/B* | 4 to 8 P/B* |
| Formula 38 | 4 to 20 | 4 to 20 P/B* | 4 to 12.5 P/B* | 4 to 8 P/B* |
| Formula 39 | 4 to 20 | 4 to 20 P/B* | 4 to 12.5 P/B* | 4 to 8 P/B* |
| Formula 40 | 4 to 20 | 4 to 20 P/B* | 4 to 12.5 P/B* | 4 to 8 P/B* |
| Formula 41 | 4 to 20 | 4 to 20 P/B* | 4 to 12.5 P/B* | 4 to 8 P/B* |
| Formula 42 | 4 to 20 | 4 to 20 P/B* | 4 to 12.5 P/B* | 4 to 8 P/B* |
| Formula 43 | 4 to 20 | 4 to 20 P/B* | 4 to 12.5 P/B* | 4 to 8 P/B* |
| Formula 44 | 4 to 20 | 4 to 20 P/B* | 4 to 12.5 P/B* | 4 to 8 P/B* |
| Formula 45 | 4 to 20 | 4 to 20 P/B* | 4 to 12.5 P/B* | 4 to 8 P/B* |
| Formula 46 | 4 to 20 | 4 to 20 P/B* | 4 to 12.5 P/B* | 4 to 8 P/B* |
| Formula 47 | 4 to 20 | 4 to 20 P/B* | 4 to 12.5 P/B* | 4 to 8 P/B* |
| Formula 48 | 4 to 20 | 4 to 20 P/B* | 4 to 12.5 P/B* | 4 to 8 P/B* |
| Formula 49 | 4 to 20 | 4 to 20 P/B* | 4 to 12.5 P/B* | 4 to 8 P/B* |
| Formula 50 | 4 to 20 | 4 to 20 P/B* | 4 to 12.5 P/B* | 4 to 8 P/B* |
| Formula 51 | 4 to 20 | 4 to 20 P/B* | 4 to 12.5 P/B* | 4 to 8 P/B* |
| Formula 52 | 4 to 20 | 4 to 20 P/B* | 4 to 12.5 P/B* | 4 to 8 P/B* |
| Formula 53 | 4 to 20 | 4 to 20 P/B* | 4 to 12.5 P/B* | 4 to 8 P/B* |
| Formula 54 | 4 to 20 | 4 to 20 P/B* | 4 to 12.5 P/B* | 4 to 8 P/B* |
| Formula 55 | 4 to 20 | 4 to 20 P/B* | 4 to 12.5 P/B* | 4 to 8 P/B* |
| Formula 56 | 4 to 20 | 4 to 20 P/B* | 4 to 12.5 P/B* | 4 to 8 P/B* |
| Formula 57 | 4 to 20 | 4 to 20 P/B* | 4 to 12.5 P/B* | 4 to 8 P/B* |
| Formula 58 | 4 to 20 | 4 to 20 P/B* | 4 to 12.5 P/B* | 4 to 8 P/B* |
| Formula 59 | 4 to 20 | 4 to 20 P/B* | 4 to 12.5 P/B* | 4 to 8 P/B* |
| Formula 60 | 4 to 20 | 4 to 20 P/B* | 4 to 12.5 P/B* | 4 to 8 P/B* |
| Formula 61 | 4 to 20 | 4 to 20 P/B* | 4 to 12.5 P/B* | 4 to 8 P/B* |
| Formula 62 | 4 to 20 | 4 to 20 P/B* | 4 to 12.5 P/B* | 4 to 8 P/B* |
| Formula 63 | 4 to 20 | 4 to 20 P/B* | 4 to 12.5 P/B* | 4 to 8 P/B* |
| Formula 64 | 4 to 20 | 4 to 20 P/B* | 4 to 12.5 P/B* | 4 to 8 P/B* |
| Formula 65 | 4 to 20 | 4 to 20 P/B* | 4 to 12.5 P/B* | 4 to 8 P/B* |
| Formula 66 | 4 to 20 | 4 to 20 P/B* | 4 to 12.5 P/B* | 4 to 8 P/B* |
| Formula 67 | 4 to 20 | 4 to 20 P/B* | 4 to 12.5 P/B* | 4 to 8 P/B* |
| Formula 68 | 4 to 20 | 4 to 20 P/B* | 4 to 12.5 P/B* | 4 to 8 P/B* |
| Formula 69 | 4 to 20 | 4 to 20 P/B* | 4 to 12.5 P/B* | 4 to 8 P/B* |
| Formula 70 | 4 to 20 | 4 to 20 P/B* | 4 to 12.5 P/B* | 4 to 8 P/B* |
| Formula 71 | 4 to 20 | 4 to 20 P/B* | 4 to 12.5 P/B* | 4 to 8 P/B* |
| Formula 72 | 4 to 20 | 4 to 20 P/B* | 4 to 12.5 P/B* | 4 to 8 P/B* |
| Formula 73 | 4 to 20 | 4 to 20 P/B* | 4 to 12.5 P/B* | 4 to 8 P/B* |
| Formula 74 | 4 to 20 | 4 to 20 P/B* | 4 to 12.5 P/B* | 4 to 8 P/B* |
| Formula 75 | 4 to 20 | 4 to 20 P/B* | 4 to 12.5 P/B* | 4 to 8 P/B* |
| Formula 76 | 4 to 20 | 4 to 20 P/B* | 4 to 12.5 P/B* | 4 to 8 P/B* |
| Formula 77 | 4 to 20 | 4 to 20 P/B* | 4 to 12.5 P/B* | 4 to 8 P/B* |
| Formula 78 | 4 to 20 | 4 to 20 P/B* | 4 to 12.5 P/B* | 4 to 8 P/B* |
| Formula 79 | 4 to 20 | 4 to 20 P/B* | 4 to 12.5 P/B* | 4 to 8 P/B* |
| Formula 80 | 4 to 20 | 4 to 20 P/B* | 4 to 12.5 P/B* | 4 to 8 P/B* |
| Formula 81 | 4 to 20 | 4 to 20 P/B* | 4 to 12.5 P/B* | 4 to 8 P/B* |
| Formula 82 | 4 to 20 | 4 to 20 P/B* | 4 to 12.5 P/B* | 4 to 8 P/B* |
| Formula 83 | 4 to 20 | 4 to 20 P/B* | 4 to 12.5 P/B* | 4 to 8 P/B* |
| Formula 84 | 4 to 20 | 4 to 20 P/B* | 4 to 12.5 P/B* | 4 to 8 P/B* |
| Formula 85 | 4 to 20 | 4 to 20 P/B* | 4 to 12.5 P/B* | 4 to 8 P/B* |
| Formula 86 | 4 to 20 | 4 to 20 P/B* | 4 to 12.5 P/B* | 4 to 8 P/B* |
| Formula 87 | 4 to 20 | 4 to 20 P/B* | 4 to 12.5 P/B* | 4 to 8 P/B* |
| Formula 88 | 4 to 20 | 4 to 20 P/B* | 4 to 12.5 P/B* | 4 to 8 P/B* |
| Formula 89 | 4 to 20 | 4 to 20 P/B* | 4 to 12.5 P/B* | 4 to 8 P/B* |
| Formula 90 | 4 to 20 | 4 to 20 P/B* | 4 to 12.5 P/B* | 4 to 8 P/B* |
| Formula 91 | 4 to 20 | 4 to 20 P/B* | 4 to 12.5 P/B* | 4 to 8 P/B* |
| Formula 92 | 4 to 20 | 4 to 20 P/B* | 4 to 12.5 P/B* | 4 to 8 P/B* |
| Formula 93 | 4 to 20 | 4 to 20 P/B* | 4 to 12.5 P/B* | 4 to 8 P/B* |
| Formula 94 | 4 to 20 | 4 to 20 P/B* | 4 to 12.5 P/B* | 4 to 8 P/B* |
| Formula 95 | 4 to 20 | 4 to 20 P/B* | 4 to 12.5 P/B* | 4 to 8 P/B* |
| Formula 96 | 4 to 20 | 4 to 20 P/B* | 4 to 12.5 P/B* | 4 to 8 P/B* |
| Formula 97 | 4 to 20 | 4 to 20 P/B* | 4 to 12.5 P/B* | 4 to 8 P/B* |
| Formula 98 | 4 to 20 | 4 to 20 P/B* | 4 to 12.5 P/B* | 4 to 8 P/B* |
| Formula 99 | 4 to 20 | 4 to 20 P/B* | 4 to 12.5 P/B* | 4 to 8 P/B* |
| Formula 100 | 4 to 20 | 4 to 20 P/B* | 4 to 12.5 P/B* | 4 to 8 P/B* |

*"P/B" corresponds to a propane/butane mixture

In the following table 2, the indication "50 to 200 wt %" corresponds to the addition of propellant to the cosmetic preparation a) in a quantity of about 50 to about 200 wt % of the weight of the cosmetic preparation a). In other words, in this cosmetic product, the cosmetic preparation a) and the propellant b) are present in a weight ratio from 100:50 to 100:200 or from 2:1 to 1:2.

Accordingly, line 4, column 3 of the following table 2 describes a mixture of the propellant-free cosmetic preparation a) according to formula 3 with a propane/butane mixture. The entry on line 4, column 3 therefore describes a cosmetic product for temporarily shaping keratinic fibers, comprising
a) a cosmetic preparation containing
 a1) about 0.5 to about 8.0 wt % of at least one copolymer that is constructed from at least the following monomer units:
  (meth)acrylic acid
  (meth)acrylic acid alkyl ester
  (meth)acrylic acid hydroxy alkyl ester;
 a2) about 0.5 to about 8.0 wt % of at least one copolymer that is constructed from at least the following monomer units:
  styrene
  acrylic acid and/or methacrylic acid,
b) propellant from the group propane/butane mixtures, wherein the proportion by weight of the copolymers a1) and a2) with respect to the total weight of the cosmetic preparation is about 1.0 to about 10 wt % and the weight ratio of cosmetic preparation a) to propellant b) is about 2:1 to about 1:2.

A second group of especially preferred cosmetic products as contemplated herein contains, with respect to their total weight; about 30 to about 70 wt % of the cosmetic preparation a) and about 30 to about 70 wt % propellant b). Such products are particularly suitable for use as a spray:

TABLE 2

| | Propellant [wt %] | | | |
|---|---|---|---|---|
| Formula 1 | 50 to 200 | 50 to 200 P/B* | 50 to 200 DFE** | 50 to 200 DME*** |
| Formula 2 | 50 to 200 | 50 to 200 P/B* | 50 to 200 DFE** | 50 to 200 DME*** |
| Formula 3 | 50 to 200 | 50 to 200 P/B* | 50 to 200 DFE** | 50 to 200 DME*** |
| Formula 4 | 50 to 200 | 50 to 200 P/B* | 50 to 200 DFE** | 50 to 200 DME*** |
| Formula 5 | 50 to 200 | 50 to 200 P/B* | 50 to 200 DFE** | 50 to 200 DME*** |
| Formula 6 | 50 to 200 | 50 to 200 P/B* | 50 to 200 DFE** | 50 to 200 DME*** |
| Formula 7 | 50 to 200 | 50 to 200 P/B* | 50 to 200 DFE** | 50 to 200 DME*** |
| Formula 8 | 50 to 200 | 50 to 200 P/B* | 50 to 200 DFE** | 50 to 200 DME*** |
| Formula 9 | 50 to 200 | 50 to 200 P/B* | 50 to 200 DFE** | 50 to 200 DME*** |
| Formula 10 | 50 to 200 | 50 to 200 P/B* | 50 to 200 DFE** | 50 to 200 DME*** |
| Formula 11 | 50 to 200 | 50 to 200 P/B* | 50 to 200 DFE** | 50 to 200 DME*** |
| Formula 12 | 50 to 200 | 50 to 200 P/B* | 50 to 200 DFE** | 50 to 200 DME*** |
| Formula 13 | 50 to 200 | 50 to 200 P/B* | 50 to 200 DFE** | 50 to 200 DME*** |
| Formula 14 | 50 to 200 | 50 to 200 P/B* | 50 to 200 DFE** | 50 to 200 DME*** |
| Formula 15 | 50 to 200 | 50 to 200 P/B* | 50 to 200 DFE** | 50 to 200 DME*** |

TABLE 2-continued

| | Propellant [wt %] | | | |
|---|---|---|---|---|
| Formula 16 | 50 to 200 | 50 to 200 P/B* | 50 to 200 DFE** | 50 to 200 DME*** |
| Formula 17 | 50 to 200 | 50 to 200 P/B* | 50 to 200 DFE** | 50 to 200 DME*** |
| Formula 18 | 50 to 200 | 50 to 200 P/B* | 50 to 200 DFE** | 50 to 200 DME*** |
| Formula 19 | 50 to 200 | 50 to 200 P/B* | 50 to 200 DFE** | 50 to 200 DME*** |
| Formula 20 | 50 to 200 | 50 to 200 P/B* | 50 to 200 DFE** | 50 to 200 DME*** |
| Formula 21 | 50 to 200 | 50 to 200 P/B* | 50 to 200 DFE** | 50 to 200 DME*** |
| Formula 22 | 50 to 200 | 50 to 200 P/B* | 50 to 200 DFE** | 50 to 200 DME*** |
| Formula 23 | 50 to 200 | 50 to 200 P/B* | 50 to 200 DFE** | 50 to 200 DME*** |
| Formula 24 | 50 to 200 | 50 to 200 P/B* | 50 to 200 DFE** | 50 to 200 DME*** |
| Formula 25 | 50 to 200 | 50 to 200 P/B* | 50 to 200 DFE** | 50 to 200 DME*** |
| Formula 26 | 50 to 200 | 50 to 200 P/B* | 50 to 200 DFE** | 50 to 200 DME*** |
| Formula 27 | 50 to 200 | 50 to 200 P/B* | 50 to 200 DFE** | 50 to 200 DME*** |
| Formula 28 | 50 to 200 | 50 to 200 P/B* | 50 to 200 DFE** | 50 to 200 DME*** |
| Formula 29 | 50 to 200 | 50 to 200 P/B* | 50 to 200 DFE** | 50 to 200 DME*** |
| Formula 30 | 50 to 200 | 50 to 200 P/B* | 50 to 200 DFE** | 50 to 200 DME*** |
| Formula 31 | 50 to 200 | 50 to 200 P/B* | 50 to 200 DFE** | 50 to 200 DME*** |
| Formula 32 | 50 to 200 | 50 to 200 P/B* | 50 to 200 DFE** | 50 to 200 DME*** |
| Formula 33 | 50 to 200 | 50 to 200 P/B* | 50 to 200 DFE** | 50 to 200 DME*** |
| Formula 34 | 50 to 200 | 50 to 200 P/B* | 50 to 200 DFE** | 50 to 200 DME*** |
| Formula 35 | 50 to 200 | 50 to 200 P/B* | 50 to 200 DFE** | 50 to 200 DME*** |
| Formula 36 | 50 to 200 | 50 to 200 P/B* | 50 to 200 DFE** | 50 to 200 DME*** |
| Formula 37 | 50 to 200 | 50 to 200 P/B* | 50 to 200 DFE** | 50 to 200 DME*** |
| Formula 38 | 50 to 200 | 50 to 200 P/B* | 50 to 200 DFE** | 50 to 200 DME*** |
| Formula 39 | 50 to 200 | 50 to 200 P/B* | 50 to 200 DFE** | 50 to 200 DME*** |
| Formula 40 | 50 to 200 | 50 to 200 P/B* | 50 to 200 DFE** | 50 to 200 DME*** |
| Formula 41 | 50 to 200 | 50 to 200 P/B* | 50 to 200 DFE** | 50 to 200 DME*** |
| Formula 42 | 50 to 200 | 50 to 200 P/B* | 50 to 200 DFE** | 50 to 200 DME*** |
| Formula 43 | 50 to 200 | 50 to 200 P/B* | 50 to 200 DFE** | 50 to 200 DME*** |
| Formula 44 | 50 to 200 | 50 to 200 P/B* | 50 to 200 DFE** | 50 to 200 DME*** |
| Formula 45 | 50 to 200 | 50 to 200 P/B* | 50 to 200 DFE** | 50 to 200 DME*** |
| Formula 46 | 50 to 200 | 50 to 200 P/B* | 50 to 200 DFE** | 50 to 200 DME*** |
| Formula 47 | 50 to 200 | 50 to 200 P/B* | 50 to 200 DFE** | 50 to 200 DME*** |
| Formula 48 | 50 to 200 | 50 to 200 P/B* | 50 to 200 DFE** | 50 to 200 DME*** |
| Formula 49 | 50 to 200 | 50 to 200 P/B* | 50 to 200 DFE** | 50 to 200 DME*** |
| Formula 50 | 50 to 200 | 50 to 200 P/B* | 50 to 200 DFE** | 50 to 200 DME*** |
| Formula 51 | 50 to 200 | 50 to 200 P/B* | 50 to 200 DFE** | 50 to 200 DME*** |
| Formula 52 | 50 to 200 | 50 to 200 P/B* | 50 to 200 DFE** | 50 to 200 DME*** |
| Formula 53 | 50 to 200 | 50 to 200 P/B* | 50 to 200 DFE** | 50 to 200 DME*** |
| Formula 54 | 50 to 200 | 50 to 200 P/B* | 50 to 200 DFE** | 50 to 200 DME*** |
| Formula 55 | 50 to 200 | 50 to 200 P/B* | 50 to 200 DFE** | 50 to 200 DME*** |
| Formula 56 | 50 to 200 | 50 to 200 P/B* | 50 to 200 DFE** | 50 to 200 DME*** |
| Formula 57 | 50 to 200 | 50 to 200 P/B* | 50 to 200 DFE** | 50 to 200 DME*** |
| Formula 58 | 50 to 200 | 50 to 200 P/B* | 50 to 200 DFE** | 50 to 200 DME*** |
| Formula 59 | 50 to 200 | 50 to 200 P/B* | 50 to 200 DFE** | 50 to 200 DME*** |
| Formula 60 | 50 to 200 | 50 to 200 P/B* | 50 to 200 DFE** | 50 to 200 DME*** |
| Formula 61 | 50 to 200 | 50 to 200 P/B* | 50 to 200 DFE** | 50 to 200 DME*** |
| Formula 62 | 50 to 200 | 50 to 200 P/B* | 50 to 200 DFE** | 50 to 200 DME*** |
| Formula 63 | 50 to 200 | 50 to 200 P/B* | 50 to 200 DFE** | 50 to 200 DME*** |
| Formula 64 | 50 to 200 | 50 to 200 P/B* | 50 to 200 DFE** | 50 to 200 DME*** |
| Formula 65 | 50 to 200 | 50 to 200 P/B* | 50 to 200 DFE** | 50 to 200 DME*** |
| Formula 66 | 50 to 200 | 50 to 200 P/B* | 50 to 200 DFE** | 50 to 200 DME*** |
| Formula 67 | 50 to 200 | 50 to 200 P/B* | 50 to 200 DFE** | 50 to 200 DME*** |
| Formula 68 | 50 to 200 | 50 to 200 P/B* | 50 to 200 DFE** | 50 to 200 DME*** |
| Formula 69 | 50 to 200 | 50 to 200 P/B* | 50 to 200 DFE** | 50 to 200 DME*** |
| Formula 70 | 50 to 200 | 50 to 200 P/B* | 50 to 200 DFE** | 50 to 200 DME*** |
| Formula 71 | 50 to 200 | 50 to 200 P/B* | 50 to 200 DFE** | 50 to 200 DME*** |
| Formula 72 | 50 to 200 | 50 to 200 P/B* | 50 to 200 DFE** | 50 to 200 DME*** |
| Formula 73 | 50 to 200 | 50 to 200 P/B* | 50 to 200 DFE** | 50 to 200 DME*** |
| Formula 74 | 50 to 200 | 50 to 200 P/B* | 50 to 200 DFE** | 50 to 200 DME*** |
| Formula 75 | 50 to 200 | 50 to 200 P/B* | 50 to 200 DFE** | 50 to 200 DME*** |
| Formula 76 | 50 to 200 | 50 to 200 P/B* | 50 to 200 DFE** | 50 to 200 DME*** |
| Formula 77 | 50 to 200 | 50 to 200 P/B* | 50 to 200 DFE** | 50 to 200 DME*** |
| Formula 78 | 50 to 200 | 50 to 200 P/B* | 50 to 200 DFE** | 50 to 200 DME*** |
| Formula 79 | 50 to 200 | 50 to 200 P/B* | 50 to 200 DFE** | 50 to 200 DME*** |
| Formula 80 | 50 to 200 | 50 to 200 P/B* | 50 to 200 DFE** | 50 to 200 DME*** |
| Formula 81 | 50 to 200 | 50 to 200 P/B* | 50 to 200 DFE** | 50 to 200 DME*** |
| Formula 82 | 50 to 200 | 50 to 200 P/B* | 50 to 200 DFE** | 50 to 200 DME*** |
| Formula 83 | 50 to 200 | 50 to 200 P/B* | 50 to 200 DFE** | 50 to 200 DME*** |
| Formula 84 | 50 to 200 | 50 to 200 P/B* | 50 to 200 DFE** | 50 to 200 DME*** |
| Formula 85 | 50 to 200 | 50 to 200 P/B* | 50 to 200 DFE** | 50 to 200 DME*** |
| Formula 86 | 50 to 200 | 50 to 200 P/B* | 50 to 200 DFE** | 50 to 200 DME*** |
| Formula 87 | 50 to 200 | 50 to 200 P/B* | 50 to 200 DFE** | 50 to 200 DME*** |
| Formula 88 | 50 to 200 | 50 to 200 P/B* | 50 to 200 DFE** | 50 to 200 DME*** |
| Formula 89 | 50 to 200 | 50 to 200 P/B* | 50 to 200 DFE** | 50 to 200 DME*** |
| Formula 90 | 50 to 200 | 50 to 200 P/B* | 50 to 200 DFE** | 50 to 200 DME*** |
| Formula 91 | 50 to 200 | 50 to 200 P/B* | 50 to 200 DFE** | 50 to 200 DME*** |
| Formula 92 | 50 to 200 | 50 to 200 P/B* | 50 to 200 DFE** | 50 to 200 DME*** |
| Formula 93 | 50 to 200 | 50 to 200 P/B* | 50 to 200 DFE** | 50 to 200 DME*** |

TABLE 2-continued

| | | Propellant [wt %] | | |
|---|---|---|---|---|
| Formula 94 | 50 to 200 | 50 to 200 P/B* | 50 to 200 DFE** | 50 to 200 DME*** |
| Formula 95 | 50 to 200 | 50 to 200 P/B* | 50 to 200 DFE** | 50 to 200 DME*** |
| Formula 96 | 50 to 200 | 50 to 200 P/B* | 50 to 200 DFE** | 50 to 200 DME*** |
| Formula 97 | 50 to 200 | 50 to 200 P/B* | 50 to 200 DFE** | 50 to 200 DME*** |
| Formula 98 | 50 to 200 | 50 to 200 P/B* | 50 to 200 DFE** | 50 to 200 DME*** |
| Formula 99 | 50 to 200 | 50 to 200 P/B* | 50 to 200 DFE** | 50 to 200 DME*** |
| Formula 100 | 50 to 200 | 50 to 200 P/B* | 50 to 200 DFE** | 50 to 200 DME*** |

*"P/B" corresponds to a propane/butane mixture
**"DFE" corresponds to 1,1-difluoroethane
***"DME" corresponds to dimethyl ether Some vessels that are worthy of consideration as pressurized gas containers for aerosol applications are those made of metal (aluminum, tinplate, tin), protected or non-splitting plastic or of glass that is coated with plastic on the outside, with compressive and breaking strength, corrosion resistance, ease of fillability as well as aesthetic aspects, manageability, printability, etc., playing a role in the selection thereof. Special inner protective paints ensure corrosion resistance in relation to the cosmetic product a).

If the products as contemplated herein are to be sprayed onto the hair, these products are advantageously provided with a dispensing device and a spray valve. The resulting cosmetic products thus comprise a cosmetic product as contemplated herein as well as a dispensing device with spray valve.

In a preferred embodiment of the disclosure, the valve has a valve cone coated with a paint or a polymeric plastic A and such a flexible element with return characteristic that returns the valve to the closed position (=idle position of the valve) upon completion of actuation. Corresponding cosmetic products in which the aerosol dispensing device comprises a valve having a valve cone and/or a flexible element with return characteristic that is/are coated with a paint or a polymeric plastic A are preferred as contemplated herein.

In another preferred embodiment of the disclosure, the valve has a flexible element with return characteristic and/or a valve cone made of at least one plastic B, preferably an elastomeric plastic. Here as well, cosmetic products as contemplated herein in which the valve has a flexible element with return characteristic and/or a valve cone made of at least one plastic B, with preferred plastics B being elastomeric plastics. Especially preferred elastomeric plastics are selected from Buna, particularly Buna N, Buna 421, Buna 1602 and Buna KA 6712, neoprene, butyl and chlorobutyl.

In another preferred embodiment of the disclosure, the flexible element with return characteristic can be embodied as a spiral spring or helical compression spring. In another preferred embodiment of the disclosure, the flexible element with return characteristic can be integrally formed with the valve cone and have bendable legs.

As pointed out at the outset, the previously described cosmetic products are characterized by special cosmetic hair characteristics, particularly advantageous characteristics in the temporary hair-shaping. A second object of the present application is therefore the use of a product as contemplated herein for temporarily shaping keratin-containing fibers, particularly human hair.

A third object of the present application is a method for temporarily shaping keratin-containing fibers, particularly human hair, in which the keratin-containing fibers are loaded with a cosmetic product as contemplated herein and fixed temporarily in their shape.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. A cosmetic product for temporarily shaping keratinic fibers, comprising:
   a cosmetic preparation containing:
      at least one copolymer a1) that is constructed from at least 90 wt % of the following monomer units based on the total weight of the copolymer a1);
         (meth)acrylic acid,
         (meth)acrylic acid alkyl ester, and
         (meth)acrylic acid hydroxy alkyl ester; and
      at least one copolymer a2) that is constructed from at least 90 wt % of the following monomer units based on the total weight of the copolymer a2);
         styrene,
         at least one of acrylic acid and/or methacrylic acid; and
         acrylic acid ester and/or methacrylic acid ester;
      wherein the proportion by weight of copolymers a1) and a2) with respect to the total weight of the cosmetic preparation is about 1.0 to about 10 wt %; and
      wherein the weight ratio of copolymer a1) to copolymer a2) is from about 1:3 to about 3:1.

2. The cosmetic product as set forth in claim 1, wherein the proportion by weight of copolymers a1) and a2) with respect to the total weight of the cosmetic preparation is about 1.5 and about 9.0 wt %.

3. The cosmetic product as set forth in claim 1, wherein the preparation contains, with respect to its total weight, about 0.1 to about 9.9 wt % of copolymer a1).

4. The cosmetic product as set forth in claim 1, wherein the preparation contains, with respect to its total weight, about 0.1 to about 9.9 wt % of copolymer a2).

5. The cosmetic product as set forth in claim 1, wherein the weight ratio of copolymer a1) to copolymer a2) is from about 1:7 to about 7:1.

6. The cosmetic product as set forth in claim 1, wherein the product further comprises at least one propellant.

7. A comprehensive product, comprising:
a cosmetic product as set forth in claim 1; and
a dispensing device with spray valve.

8. The cosmetic product as set forth in claim 1, wherein the proportion by weight of copolymers a1) and a2) with respect to the total weight of the cosmetic preparation is about 2.0 and about 8.0 wt %.

9. The cosmetic product as set forth in claim 1, wherein the preparation contains, with respect to its total weight, about 0.5 to about 8.5 wt % of copolymer a1).

10. The cosmetic product as set forth in claim 1, wherein the preparation contains, with respect to its total weight, about 1.0 to about 7.0 wt % of copolymer a1).

11. The cosmetic product as set forth in claim 1, wherein the preparation contains, with respect to its total weight, about 0.5 to about 8.5 wt % of copolymer a2).

12. The cosmetic product as set forth in claim 1, wherein the preparation contains, with respect to its total weight, about 1.0 to about 7.0 wt % of copolymer a2).

13. The cosmetic product as set forth in claim 1, wherein the cosmetic preparation further comprises at least one thickener from the group with the INCI designations acrylates/beheneth-25 methacrylate copolymer, acrylates/ceteth-20 itaconate copolymer, acrylates/ceteth-20 methacrylate copolymer, acrylates/laureth-25 methacrylate copolymer, acrylates/palmeth-20 acrylate copolymer, acrylates/palmeth-25 acrylate copolymer, acrylates/palmeth-25 itaconate copolymer and acrylates/steareth-50 acrylate copolymer.

14. The cosmetic product as set forth in claim 1, wherein the preparation contains, with respect to its total weight, 0.05 to 8.0 wt % of a thickener.

15. The cosmetic product as set forth in claim 1, wherein the copolymer a1) bears the INCI designation acrylates/hydroxyesters acrylates copolymer.

16. The cosmetic product as set forth in claim 1, wherein:
the at least one copolymer a1) is constructed from at least 97 wt % of the following monomer units based on the total weight of the copolymer a1);
(meth)acrylic acid,
(meth)acrylic acid alkyl ester, and
(meth)acrylic acid hydroxy alkyl ester; and
the at least one copolymer a2) is constructed from at least 97 wt % of the following monomer units based on the total weight of the copolymer a2);
styrene,
at least one of acrylic acid and/or methacrylic acid; and
acrylic acid ester and/or methacrylic acid ester.

17. A cosmetic product for temporarily shaping keratinic fibers, comprising:
a cosmetic preparation containing:
at least one copolymer a1) that is constructed from at least 90 wt % of the following monomer units based on the total weight of the copolymer a1);
(meth)acrylic acid,
(meth)acrylic acid alkyl ester, and
(meth)acrylic acid hydroxy alkyl ester;
at least one copolymer a2) that is constructed from at least 90 wt % of the following monomer units based on the total weight of the copolymer a2);
styrene,
at least one of acrylic acid and/or methacrylic acid; and
acrylic acid ester and/or methacrylic acid ester;
at least one propellant from the group propane, mixture of propane and butane, dimethyl ether and 1,1-difluoroethane; and
ethanol;
wherein the proportion by weight of copolymers a1) and a2) with respect to the total weight of the cosmetic preparation is about 1.0 to about 10 wt %; and
wherein the weight ratio of copolymer a1) to copolymer a2) is from about 1:3 to about 3:1.

18. A method for temporarily shaping keratin-containing fibers, the method comprising the steps of:
loading keratin-containing fibers with a cosmetic product comprising:
at least one copolymer a1) that is constructed from at least 90 wt % of the following monomer units based on the total weight of the copolymer a1);
(meth)acrylic acid,
(meth)acrylic acid alkyl ester, and
(meth)acrylic acid hydroxy alkyl ester; and
at least one copolymer a2) that is constructed from at least 90 wt % of the following monomer units based on the total weight of the copolymer a2);
styrene,
at least one of acrylic acid and/or methacrylic acid; and
acrylic acid ester and/or methacrylic acid ester;
wherein the proportion by weight of copolymers a1) and a2) with respect to the total weight of the cosmetic product is about 1.0 to about 10 wt %; and
wherein the weight ratio of copolymer a1) to copolymer a2) is from about 1:3 to about 3:1; and
temporarily fixing the keratin-containing fibers into shape.

* * * * *